(12) United States Patent
Ploch et al.

(10) Patent No.: US 11,406,762 B2
(45) Date of Patent: Aug. 9, 2022

(54) DRUG DELIVERY DEVICE

(71) Applicant: SANOFI, Paris (FR)

(72) Inventors: Markus Ploch, Frankfurt am Main (DE); Aled Meredydd James, Warwick (GB); Anthony Paul Morris, Warwick (GB); Matthew Meredith Jones, Warwick (GB); Oliver Charles Gazeley, Warwick (GB); Robert Veasey, Warwick (GB); David Aubrey Plumptre, Warwick (GB)

(73) Assignee: Sanofi, Paris (FR)

( * ) Notice: Subject to any disclaimer, the term of this patent is extended or adjusted under 35 U.S.C. 154(b) by 778 days.

(21) Appl. No.: 16/312,204

(22) PCT Filed: Jun. 30, 2017

(86) PCT No.: PCT/EP2017/066295
§ 371 (c)(1),
(2) Date: Dec. 20, 2018

(87) PCT Pub. No.: WO2018/002313
PCT Pub. Date: Jan. 4, 2018

(65) Prior Publication Data
US 2019/0231979 A1    Aug. 1, 2019

(30) Foreign Application Priority Data

Jul. 1, 2016  (EP) .................................. 16305828

(51) Int. Cl.
*A61M 5/24*    (2006.01)
*A61M 5/315*    (2006.01)

(52) U.S. Cl.
CPC ............ *A61M 5/24* (2013.01); *A61M 5/2422* (2013.01); *A61M 5/31583* (2013.01);
(Continued)

(58) Field of Classification Search
CPC .. A61M 5/24; A61M 5/2422; A61M 5/31535; A61M 5/3155; A61M 5/31551;
(Continued)

(56) References Cited

U.S. PATENT DOCUMENTS

2004/0210199 A1* 10/2004 Atterbury ................ G01D 5/25
                                                                   604/224
2008/0287883 A1   11/2008 Radmer et al.
2016/0074588 A1    3/2016 Butler et al.

FOREIGN PATENT DOCUMENTS

JP      2008-521534      6/2008
JP      2015-521072      7/2015
(Continued)

OTHER PUBLICATIONS

International Preliminary Report on Patentability in Application No. PCT/EP2017/066295, dated Jan. 1, 2019, 6 pages.
(Continued)

*Primary Examiner* — Shefali D Patel
(74) *Attorney, Agent, or Firm* — Fish & Richardson P.C.

(57) ABSTRACT

A drug delivery device comprising a housing body; a piston rod configured to rotate in a rotational direction during dose dispensing under a driving force; and a threaded insert, wherein the piston rod is in threaded engagement with the threaded insert such that during the dose dispensing. the piston rod displaces axially in a distal direction relative to the threaded insert for displacement of a cartridge hung. The threaded insert is movable relative to a stop provided in the housing body and a spring is provided to bias the threaded insert against the stop so that the rotation of the piston rod causes the threaded insert to move away from the stop in response to reaction forces, induced by the cartridge bung into the threaded insert, acting on the piston rod in a (Continued)

proximal direction when the reaction forces exceed a biasing force of the spring.

15 Claims, 4 Drawing Sheets

Specification includes a Sequence Listing.

(52) U.S. Cl.
CPC ..... *A61M 5/31535* (2013.01); *A61M 5/31551* (2013.01); *A61M 2005/2403* (2013.01); *A61M 2005/2407* (2013.01)

(58) Field of Classification Search
CPC ............ A61M 5/31566; A61M 5/3157; A61M 5/31583; A61M 5/31585; A61M 2005/2403; A61M 2005/2407; A61M 2005/3125; A61M 2205/582; A61M 2205/583

See application file for complete search history.

(56) References Cited

FOREIGN PATENT DOCUMENTS

| WO | WO 2006/058883 | 6/2006 | |
|----|----|----|----|
| WO | WO 2013/178602 | 12/2013 | |
| WO | WO 2015/036345 | 3/2015 | |
| WO | WO 2016/055628 | 4/2016 | |
| WO | WO-2016055627 A1 * | 4/2016 | ........ A61M 5/31585 |

OTHER PUBLICATIONS

International Search Report and Written Opinion in Application No. PCT/EP2017/066295, dated Oct. 10, 2017, 8 pages.

* cited by examiner

DRUG DELIVERY DEVICE

CROSS REFERENCE TO RELATED APPLICATIONS

The present application is a national stage entry of International Patent Application No. PCT/EP2017/066295, filed on Jun. 30, 2017, and claims priority to European Patent Application No. 16305828.2, filed on Jul. 1, 2016, the entire contents of each of which are incorporated herein by reference.

SEQUENCE LISTING

This application contains a Sequence Listing that has been submitted electronically as an ASCII text file named "Sequence_Listing.txt." The ASCII text file, created on Dec. 21, 2021, is 25 kilobytes in size. The material in the ASCII text file is hereby incorporated by reference in its entirety.

TECHNICAL FIELD

The present disclosure is directed to a drug delivery device.

BACKGROUND

Handheld injection device, e.g. pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

SUMMARY

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

A further differentiation of drug delivery device types refers to the drive mechanism. There are devices which are manually driven, e.g. by a user applying a force to an injection button, devices which are driven by a power source such as a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. In general, the present disclosure is applicable for all of these types of devices, i.e. for devices with or without a drive spring.

These types of pen delivery devices (so named because they often resemble an enlarged fountain pen) are generally comprised of three primary elements: a cartridge section that includes a medicament cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

Drug delivery devices of the generic kind include a housing or a housing body with said dosing section. The dosing section is the portion of the pen device that is used to set (select) a dose. Inside the housing body, a dose dispensing mechanism is housed, which includes a piston rod, a lead screw or the like that may have a bearing at its distal end. The medicament cartridge may be retained in a cartridge holder connected to the distal end of the housing or the housing body. As indicated above, the piston rod serves to displace a cartridge bung in the cartridge in a distal, resp. dispensing direction. At the distal end of the cartridge, the injection needle assembly may be attached so that the (distal) injection end of the needle cannula is in fluid communication with the medicament contained in the medicament cartridge. When the piston rod displaces the bung in distal direction, the medicament is dispensed from the cartridge through the injection needle cannula. After an injection, as generally recommended by most drug delivery device and/or needle assembly manufacturers and suppliers, the needle assembly is removed and discarded.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

In order to set a dose of the medicament to be injected, drug delivery devices comprise a dose setting mechanism. The dose setting mechanism may comprise a dosing element or dose setting member such as a dose dial sleeve, a drum scale, a number sleeve or the like. A drive element such as a drive sleeve may be configured to rotationally drive the piston rod. For auto-injectors an energy source for the driving force such a rechargeable spring may configured to be prestressed in a dose setting step, wherein in the dispensing step, the energy source is coupled to the drive element, such that the release of stored energy drives the drive sleeve which transfers the driving force to the piston rod so that the piston rod can displace the bung in the cartridge. To initiate the dispense, a dispense button or the like may be provided to trigger the dispense of a set dose.

The present disclosure is directed to a drug delivery device comprising a housing body, a piston rod configured to rotate in a first direction during dose dispensing under a driving force and a threaded insert, wherein the piston rod is in threaded engagement with the threaded insert such that during dose dispensing, the piston rod displaces axially in a distal direction relative to the threaded insert for displacement of a cartridge bung.

The subject matter disclosed in the present disclosure is in particular suitable for drug delivery devices configured for replaceable cartridges. For example, by detaching the cartridge holder from the housing body, the user may replace an empty cartridge with a new one. Then the cartridge holder may be reattached to the housing body. However, the disclosure also includes disposable drug delivery devices that are usually thrown away by the user after the content of medicament cartridge has been dispensed.

In the field of medical injection devices, there is a trend toward the use of smaller and smaller gauge cannula in the type of needle typically used for self-injection. While small gauge cannulas typically reduce the pain associated with the procedure, they can result in particular user/use-related risks. One particular risk associated with small gauge needles is an increased risk of blockage during use. Such blockage might be the result of any one of a number of causes including, but not limited to, manufacturing defects, septum coring (during piercing of a cartridge septum by the proximal tip of the needle during attachment to the device), or crystallisation of the drug formulation within the inner bore of the cannula following use. Typically, users are instructed to undertake at least one prime dose before any injection and not to re-use needles, however it is widely known that such instructions are not always adhered to. If drug delivery is attempted with a blocked or missing needle then the delivery device is typically designed to stall under the applied load, rather than fail in an uncontrolled manner. However, compliance in the cartridge and drive mechanism often mean that it is possible for the delivery mechanism (and associated dose indication means) to advance by an amount before becoming jammed. For injection devices where there is a direct mechanical connection between the force input interface (e.g. dose delivery button) and the proximal face of the bung in the medicament cartridge, for relatively large doses the user may be able to detect the increase in the reaction load at the force input interface, and also the fact that the button has not returned to its rest position. However, for devices such as auto-injectors, where there is no direct mechanical connection between the force input interface (e.g. dose delivery button) and the proximal face of the bung in the medicament cartridge, this feedback mechanism does not exist and so the user may be unaware that they have received a partial or (for doses that are comparable in size to the compliance within the system) complete underdose. For such devices, the provision of dose completion feedback based on the presence or absence of residual pressure within the cartridge, rather than on mechanical displacement alone, might provide a useful mitigation measure to address the risks posed by a blocked needle event.

In addition, users of existing known injection devices are typically advised to keep the needle in their skin for a short period of time after the end of the dispensing action (10 seconds is common). This is required to provide sufficient time for fluid to be dispensed, releasing residual pressure in the cartridge allowing any compliant components in the system to return to their pre-dose state.

The subject matter described in the present disclosure can improve the safety of known drug delivery devices, in particular, by providing a reliable indication when a blocked needle event occurs.

Known drug delivery devices have a threaded insert fixed with respect to the housing body or a threaded portion that is immobile. The piston rod has a thread which engages a corresponding thread on the threaded insert. When the piston rod rotates around a rotational axis under the driving force provided and because of the threaded engagement with the threaded insert, the piston rod rotates though the thread engagement and displaces in distal direction. The threaded insert is movable relative to a stop provided in the housing body. The stop may be formed on the housing body or may be rigidly attached to the housing body. The threaded insert is resiliently mounted in the housing body. A resilient means is provided to bias the threaded insert against the stop. Due to the ability of threaded insert to displace and because of the resilient means, rotation of the piston rod causes the threaded insert to move away from the stop in response to reaction forces acting on the piston rod in proximal direction, opposite to the distal direction, when the reaction forces exceed the biasing force of the resilient means. In particular, the above accounts for reaction forces induced from a cartridge bung into the threaded insert (via the piston rod).

As described herein, the definition of a resilient means biasing the threaded insert against the stop includes embodiments in which the resilient means exerts a force to the threaded insert only if the threaded insert does not abut the stop, whereas the force exerted by the resilient means may be zero if the threaded insert abuts the stop. However, this definition further includes embodiments in which the threaded insert is prestressed against the stop by the resilient means, i.e. embodiments in which the resilient means exerts a force to the threaded insert if the threaded insert abuts the stop and exerts a, e.g. higher, force if the threaded insert does not abut the stop.

The threaded insert can be displaced in response to reaction forces acting on the piston rod in axial direction. Such reaction forces may not only be the result of a clogged needle cannula but may also emerge from high friction forces in the cartridge that generate a reaction force opposite the axial force of the piston to displace the bung. The forces required to displace the threaded insert typically occur during every dispense because the mechanism may always apply maximum force on the bung. However, the speed may be different (and could be zero if the needle is blocked). When the piston rod is not able to displace in the axial direction as predetermined by the pitch of the threaded engagement with the threaded insert in connection with the rotation of the piston rod, then the threaded insert is forced to move away from the stop the absorb the deviation. Accordingly, when the threaded insert is at the stop position, it can be referred to as a released position and when the threaded insert is at a position away from the stop, this can be referred to as a loaded position because the threaded insert is displaced against the force of the resilient means. Displacement of the threaded insert gives a reliable indication about reaction forces induced into the piston rod and can in particular efficiently indicate a blocked needle event. A further advantage of the mechanism described in this document is that it provides a user with a more accurate indication of when the full dose has been delivered.

Preferably, the stop is fixedly provided in the housing or housing body. The stop may be a projection, a surface, an abutment or the like configured to engage a corresponding counter surface on the threaded insert. The threaded insert may be supported against the stop by the resilient member. The threaded insert has an opening with an inner thread engaging the outer thread on the piston rod. In a preferred embodiment, the threaded insert is provided as a threaded nut.

According to a further embodiment, the threaded insert is movable relative to a stop fixedly provided in the housing body and the resilient means is provided to bias the threaded insert against the stop so that rotation of the piston rod causes the threaded insert to move away from the stop such that when the required force to move the piston rod in the distal direction exceeds the driving force provided to displace the threaded insert, rotation of the piston rod causes the threaded insert to displace away from the stop.

The resilient means may be configured as a spring such as an axially acting spring, like a compression spring or a tension spring. It may also be configured as a torsion spring acting in rotational direction. Other suitable means to resiliently mount the threaded insert in the housing body are possible as well. The resilient means may be configured to bias the threaded insert against the stop in a pre-stressing manner. However, it is also possible that the resilient means is configured such that the resilient means is charged with a resilient force when the threaded insert moves away from the stop.

According to a further embodiment, the resilient means is configured to bias the threaded insert against an axial and/or a rotational stop. In this regard, one embodiment provides an axial stop and the threaded insert is axially movable with respect to the stop. The displacement of the threaded insert away from the stop, preferably in proximal direction, provides a reliable indication of the reaction forces and may in particular efficiently indicate that the driving force is not sufficient to overcome the reaction forces induced from the bung.

For providing pure axial displacement, the threaded insert may be rotationally constrained with respect to the housing or housing body. For that purpose, the threaded insert may be in splined engagement with the housing body or an insert fixed to the housing body so that the threaded insert can move relative to the housing in axial direction at least between two predefined points but wherein the threaded insert cannot rotate relative to the housing body. Splined engagement may be achieved by a number of corresponding spline features such as teeth provided on the housing and the threaded insert. When the reaction force induced into the threaded insert via the piston rod exceeds the force of the resilient or biasing means, the threaded insert is caused to move axially thereby providing a reliable indication mechanism with respect to the reaction forces.

As an alternative, the threaded insert may be rotateable with respect to the stop. The stop may be provided as a rotational stop. In this case, axial displacement of the threaded insert is not necessary. A resilient torsion element such as a torsion spring may be provided to urge the threaded insert or an abutment surface of the threaded insert against the stop surface. When the reaction force induced into the threaded insert via the piston rod exceeds the force of the torsion spring, the threaded insert is caused to rotate. This embodiment has benefits in terms of reduced space required for the mechanism and regarding in the increased size of an indicator flag possible for a given axial displacement.

In addition to pure axial and rotational displacement of the threaded insert, according to a further embodiment, the threaded insert is constrained in the housing body such as to be able to rotate, preferably through a predetermined angel of rotation, on a helical path relative to the stop. In other words, the threaded insert is connected to the housing body, e.g. engages the housing body in such way that the threaded insert displaces away from the stop in axial direction while at least over a section of the axial displacement the threaded insert also rotates relative to the stop, e.g. around a longitudinal axis of the piston rod. In this regard, a coupling may be provided between the threaded insert and the housing body, wherein the coupling is configured to translate axial displacement into rotational movement. The lead screw interface with the thread induces a torque. This will also tend to encourage the threaded insert to rotate. Said coupling may include a helically formed thread. The combination of axial and rotational displacement may be combined with an axial and/or rotational stop easily. For example, the stop may be defined by an end of the helically formed thread. This embodiment has particular benefits in terms of a reliable indication mechanism and space reduction. The helical thread coupling between the threaded insert and the housing body may have a greater pitch that the thread engagement between the threaded insert and the piston rod.

According to a further embodiment, the injection device comprises a drive sleeve configured to rotate the piston rod during a dispensing step or during dose dispensing, a rotatable dose setting member that is rotatable about a longitudinal axis of the housing and a power reservoir operably coupled to the rotatable dose setting member, wherein energy is stored in the power reservoir during rotation of the rotatable dose setting member. A release clutch is arranged between the drive sleeve and the dose setting member, wherein the release clutch is configured to allow relative rotation of the dose setting member and the drive member during dose setting and to rotationally constrain the drive member to the dose setting member during dose dispensing. To switch between dose dialing mode and dose dispensing mode, a selection member is axially moveable relative to the housing body between a first and a second axial position and is operably coupled to the drive sleeve such that in the first axial position of the selection member, preferably a proximal position, the drive sleeve is disengaged from the dose setting member and wherein in the second axial position, preferably a distal position, the drive sleeve is rotationally constrained to the dose setting member. The threaded insert is configured such that when the threaded insert is in a position away from the stop, the threaded insert prevents the selection member from returning to the first axial position. By preventing the return of the selection member, the injection device cannot return into the dose dial mode as the drive sleeve remains engaged with the dose setting member. In the state of a needle event, a reliable safety mechanism is provided.

The power reservoir may be provided in the form of a drive spring. The drive spring may be charged by rotation of the dose setting member. The energy stored in the drive spring during said charging should regularly be sufficient to provide the energy necessary to move the piston rod in distal direction so as to drive the bung in the cartridge in the distal direction such that medicament is dispensed from the cartridge. The dose setting member may be configured as a sleeve-like component, e.g. a number sleeve or a scale drum. A dose dial may be configured as a dial grip for setting user variable doses of a medicament and may be rotationally coupled to the dose setting member during dose setting.

A high degree of accuracy is achieved, when the drive spring is pre-wound or pre-charged upon assembly such that it applies a sufficient force or torque to the dose setting member when the injection device is at zero units dialed. When the user rotates the dial grip to set a dose, he rotates the dose setting member such that the drive spring is charged. By providing a minimum of force or torque, play between the loaded components is effectively prevented.

According to a further embodiment, the selection member is configured to engage the housing body in the first axial position such that the drive sleeve is rotationally constrained to the housing. In the second axial position, the selection member is configured such that the drive sleeve is rotateable relative to the housing. Thereby, the drive sleeve is rotationally constrained during dose setting (first position of selection element) such that the drive spring can be charged. During dose dispensing the drive sleeve is not rotationally constrained to the housing such that the driving force can rotate the piston rod. For that purpose, the selection member and the housing body may be provided with spline features such as teeth for mutual engagement in the first axial position of the drive sleeve.

The selection member may be formed separately from the drive sleeve. In particular, the drive sleeve may be configured such as to maintain is axial position during dose setting and dose dispensing.

According to a further embodiment, the drive sleeve is integrally formed with the selection member such that the drive sleeve constitutes the selection member. In this case, the drive sleeve is axially displaceable with respect to the housing body between a first and a second axial position, wherein in the first axial position, the drive sleeve is disengaged from the dose setting member and wherein in the second axial position, the drive sleeve is rotationally constrained to the dose setting member. The threaded insert is configured such that when the threaded insert is in a position away from the stop, the threaded insert prevents the drive sleeve from returning to the first axial position and therefore to disengaging from the dose setting member.

The drive sleeve may be configured to engage the housing body in the first axial position such that the drive sleeve is rotationally constrained to the housing, wherein the drive sleeve is rotateable relative to the housing in the second axial position. The drive sleeve and the housing may be provided with a splined interface configured such that when the drive sleeve is moved from the first into the second position, the splined interface disengages and the drive sleeve is free to rotate relative to the housing body. This releasable engagement with the housing forms a releasable clutch for dose setting and dose dispensing. The drive sleeve is further configured to engage the dose setting member in the second position such that the drive sleeve is rotationally constrained to the dose setting member. The drive sleeve and the dose setting member may be provided with corresponding teeth and/or grooves to constitute a splined tooth interface. When the drive sleeve is moved into the second, distal position, the drive sleeve is disengaged from its rotational lock with the housing and forms a rotational lock with the dose setting member, so that the charged energy of the drive spring can be directly transferred from the dose setting member to the drive sleeve.

In order to return the drive sleeve or the selection member from the second position into the first position, a spring may be provided that is configured to bias the drive sleeve and/or the selection member into the first axial position. The spring urges the drive sleeve and/or the selection member into the first axial position after release of a trigger button. Further, the spring may be configured as a clutch spring.

For efficient functional integration, the resilient means is arranged such as to bias the drive sleeve into the first axial position. Accordingly, a spring or the like may serve to bias the threaded insert against the stop and to bias the drive sleeve into the first axial position. For that purpose, the resilient element may be provided between the drive sleeve and the threaded insert.

In order to initiate the dispense of the injection device, a further embodiment of the injection device is configured such that a trigger button displaces or moves the drive sleeve and/or the selection member from the first into the second axial position when the trigger button is moved from a first into a second position.

According to a further embodiment, the injection device comprises a dial grip. The dial grip and the trigger button may be rotationally fixed but axially movable relative to each other. A clutch for releasably coupling the trigger button to the dose setting member may be provided by corresponding splined portions on the trigger button and the dose setting member, wherein axial movement of the trigger button from a first position into a second position causes the clutch to disengage. The trigger button and the dial grip may be rotationally fixed but axially movable relative to each other by means of a splined interface wherein the trigger button and the dial grip are provided with corresponding teeth and/or grooves that rotationally constrain the components to each other when engaged. By moving the trigger button from the first position into the second position, the splined interface is disconnected such that the dose setting member may rotate relative to the trigger button. This mechanism provides for a convenient actuation of the device. Thus, when the user actuates the trigger button for dispense, he disconnects the trigger button from the dose setting member, and hence the actuation element is disconnected from the driving force.

In order to prevent the drive sleeve from returning into the first axial position, the threaded insert, the housing body and the drive sleeve may each be provided with spline features such as teeth, wherein axial displacement of the drive sleeve from the first into the second position causes disengagement of the spline features of the drive sleeve from the spline features of the housing body through the spline features of the threaded insert such that the drive sleeve is free to rotate, wherein displacement of the thread insert away from the stop causes misalignment between the spline features of the threaded insert and the housing body such that the drive sleeve is prevented from returning into the first axial position. The above misalignment may be achieved by rotating the threaded insert for example. When the drive sleeve is displaced into the second position, it displaces relative to the threaded insert and the housing body.

According to a further embodiment, the threaded insert is configured to engage and to rotationally lock the drive sleeve to the threaded insert when the threaded insert is in a position away from the stop and when the drive sleeve is returned from the second towards the first axial position, e.g. after release of the trigger button and under the force of the clutch spring. This may be achieved by the spline features of the drive sleeve engaging the spline features of the threaded insert, while there is misalignment between the spline features of the threaded insert and of the housing body such that the drive sleeve is prevented from returning into the first axial position.

By rotationally constraining the drive sleeve to the threaded insert, it is possible to prevent dose setting in the case of a blocked needle as, in the second axial position of the drive sleeve, the drive sleeve is rotationally constrained to the dose setting member.

For releasably coupling the drive sleeve to the dose setting member, a further embodiment includes a clutch plate, wherein the clutch plate is rotationally constrained to the dose setting member, e.g. by a splined interface preventing relative rotational movement between the clutch plate and the dose setting member while allowing relative axial motion. The clutch plate is coupled to the drive sleeve via a ratchet interface such that the energy stored in the drive spring is prevented from being released when the drive sleeve is in the first position. The clutch plate may have a surface provided with angled teeth directly facing a surface of the drive sleeve that is provided with corresponding angled teeth. The injection device may further be provided with a clutch spring arranged such as to bias the drive sleeve and the clutch plate together and to bias the drive sleeve into the first axial position. The angled teeth of the drive sleeve and the clutch plate may be arranged such that when the surfaces contact each other, relative rotation generates an audible click. In the direction of the spring torque, the torque can be transferred from the dose setting member and the clutch plate to the drive sleeve.

Preferably, the drive sleeve is rotationally constrained to the piston rod via a splined interface. When the drive sleeve is rotated, the piston rod is forced to move axially relative to the drive sleeve due to the thread engagement with the threaded insert.

A further embodiment comprises means to provide a haptic and/or visual and/or tactile feedback to the user when the threaded insert is displaced. The housing body may be for example provided with a window, an aperture or the like arranged to provide visual confirmation of a displacement of the threaded insert. The threaded insert may be provided with a colored marking, such as a visual flag, that is only visible through a window in the housing body in the case of a blocked needle event. In that case, the threaded insert is not allowed to return to its initial released position at the stop.

According to a further embodiment, the drug delivery device comprises a cartridge containing a medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO: 1).

Exendin-4 derivatives are for example selected from the following list of compounds:

H-(Lys)4-des Pro36, des Pro37 Exendin-4(1-39)-NH2 (SEQ ID NO: 2),

H-(Lys)5-des Pro36, des Pro37 Exendin-4(1-39)-NH2 (SEQ ID NO: 3), des Pro36 Exendin-4(1-39) (SEQ ID NO: 4), des Pro36 [Asp28] Exendin-4(1-39) (SEQ ID NO: 5), des Pro36 [IsoAsp28] Exendin-4(1-39) (SEQ ID NO: 6), des Pro36 [Met(O)14, Asp28] Exendin-4(1-39) (SEQ ID NO: 7), des Pro36 [Met(O)14, IsoAsp28] Exendin-4(1-39) (SEQ ID NO: 8), des Pro36 [Trp(O2)25, Asp28] Exendin-4(1-39) (SEQ ID NO: 9), des Pro36 [Trp(O2)25, IsoAsp28] Exendin-4(1-39) (SEQ ID NO: 10), des Pro36 [Met(O)14 Trp(O2)25, Asp28] Exendin-4(1-39) (SEQ ID NO: 11), des Pro36 [Met(O)14 Trp(O2)25, IsoAsp28] Exendin-4 (1-39) (SEQ ID NO: 12); or des Pro36 [Asp28] Exendin-4(1-39) (SEQ ID NO: 5), des Pro36 [IsoAsp28] Exendin-4(1-39) (SEQ ID NO: 6), des Pro36 [Met(O)14, Asp28] Exendin-4(1-39) (SEQ ID NO: 7), des Pro36 [Met(O)14, IsoAsp28] Exendin-4(1-39) (SEQ ID NO: 8), des Pro36 [Trp(O2)25, Asp28] Exendin-4(1-39) (SEQ ID NO: 9), des Pro36 [Trp(O2)25, IsoAsp28] Exendin-4(1-39) (SEQ ID NO: 10), des Pro36 [Met(O)14 Trp(O2)25, Asp28] Exendin-4(1-39) (SEQ ID NO: 11), des Pro36 [Met(O)14 Trp(O2)25, IsoAsp28] Exendin-4 (1-39) (SEQ ID NO: 12), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010) (SEQ ID NO: 13), H-(Lys)6-des Pro36 [Asp28] Exendin-4(1-39)-Lys6-NH2 (SEQ ID NO: 14), des Asp28 Pro36, Pro37, Pro38Exendin-4(1-39)-NH2 (SEQ ID NO: 15), H-(Lys)6-des Pro36, Pro38 [Asp28] Exendin-4(1-39)-NH2 (SEQ ID NO: 16), H-Asn-(Glu)5des Pro36, Pro37, Pro38 [Asp28] Exendin-4(1-39)-NH2 (SEQ ID NO: 17), des Pro36, Pro37, Pro38 [Asp28] Exendin-4(1-39)-(Lys) 6-NH2 (SEQ ID NO: 18), H-(Lys)6-des Pro36, Pro37, Pro38 [Asp28] Exendin-4(1-39)-(Lys)6-NH2 (SEQ ID NO: 19), H-Asn-(Glu)5-des Pro36, Pro37, Pro38 [Asp28] Exendin-4(1-39)-(Lys)6-NH2 (SEQ ID NO: 20), H-(Lys)6-des Pro36 [Trp(O2)25, Asp28] Exendin-4(1-39)-Lys6-NH2 (SEQ ID NO: 21), H-des Asp28 Pro36, Pro37, Pro38 [Trp(O2)25] Exendin-4(1-39)-NH2 (SEQ ID NO: 22), H-(Lys)6-des Pro36, Pro37, Pro38 [Trp(O2)25, Asp28] Exendin-4(1-39)-NH2 (SEQ ID NO: 23), H-Asn-(Glu)5-des Pro36, Pro37, Pro38 [Trp(O2)25, Asp28] Exendin-4(1-39)-NH2 (SEQ ID NO: 24), des Pro36, Pro37, Pro38 [Trp(O2)25, Asp28] Exendin-4 (1-39)-(Lys)6-NH2 (SEQ ID NO: 25), H-(Lys)6-des Pro36, Pro37, Pro38 [Trp(O2)25, Asp28] Exendin-4(1-39)-(Lys)6-NH2 (SEQ ID NO: 26), H-Asn-(Glu)5-des Pro36, Pro37, Pro38 [Trp(O2)25, Asp28] Exendin-4(1-39)-(Lys)6-NH2 (SEQ ID NO: 27), H-(Lys)6-des Pro36 [Met(O)14, Asp28] Exendin-4(1-39)-Lys6-NH2 (SEQ ID NO: 28), des Met(O)14 Asp28 Pro36, Pro37, Pro38 Exendin-4(1-39)-NH2 (SEQ ID NO: 29), H-(Lys)6-desPro36, Pro37, Pro38 [Met(O)14, Asp28] Exendin-4(1-39)-NH2 (SEQ ID NO: 30), H-Asn-(Glu)5-des Pro36, Pro37, Pro38 [Met(O)14, Asp28] Exendin-4(1-39)-NH2 (SEQ ID NO: 31), des Pro36, Pro37, Pro38 [Met(O)14, Asp28] Exendin-4 (1-39)-(Lys)6-NH2 (SEQ ID NO: 32), H-(Lys)6-des Pro36, Pro37, Pro38 [Met(O)14, Asp28] Exendin-4(1-39)-(Lys)6-NH2 (SEQ ID NO: 33), H-Asn-(Glu)5 des Pro36, Pro37, Pro38 [Met(O)14, Asp28] Exendin-4(1-39)-(Lys)6-NH2 (SEQ ID NO: 34), H-Lys6-des Pro36 [Met(O)14, Trp(O2)25, Asp28] Exendin-4(1-39)-Lys6-NH2 (SEQ ID NO: 35), H-des Asp28 Pro36, Pro37, Pro38 [Met(O)14, Trp(O2)25] Exendin-4(1-39)-NH2 (SEQ ID NO: 36), H-(Lys)6-des Pro36, Pro37, Pro38 [Met(O)14, Asp28] Exendin-4(1-39)-NH2 (SEQ ID NO: 37), H-Asn-(Glu)5-des Pro36, Pro37, Pro38 [Met(O)14, Trp (O2)25, Asp28] Exendin-4(1-39)-NH2 (SEQ ID NO: 38), des Pro36, Pro37, Pro38 [Met(O)14, Trp(O2)25, Asp28] Exendin-4(1-39)-(Lys)6-NH2 (SEQ ID NO: 39), H-(Lys)6-des Pro36, Pro37, Pro38 [Met(O)14, Trp(O2) 25, Asp28] Exendin-4(S1-39)-(Lys)6-NH2 (SEQ ID NO: 40), H-Asn-(Glu)5-des Pro36, Pro37, Pro38 [Met(O)14, Trp (O2)25, Asp28] Exendin-4(1-39)-(Lys)6-NH2 (SEQ ID NO: 41);

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Various non-limiting, exemplary embodiments of the subject matter disclosed herein will now be described with reference to the accompanying drawings, in which.

DETAILED DESCRIPTION

Figure 1:
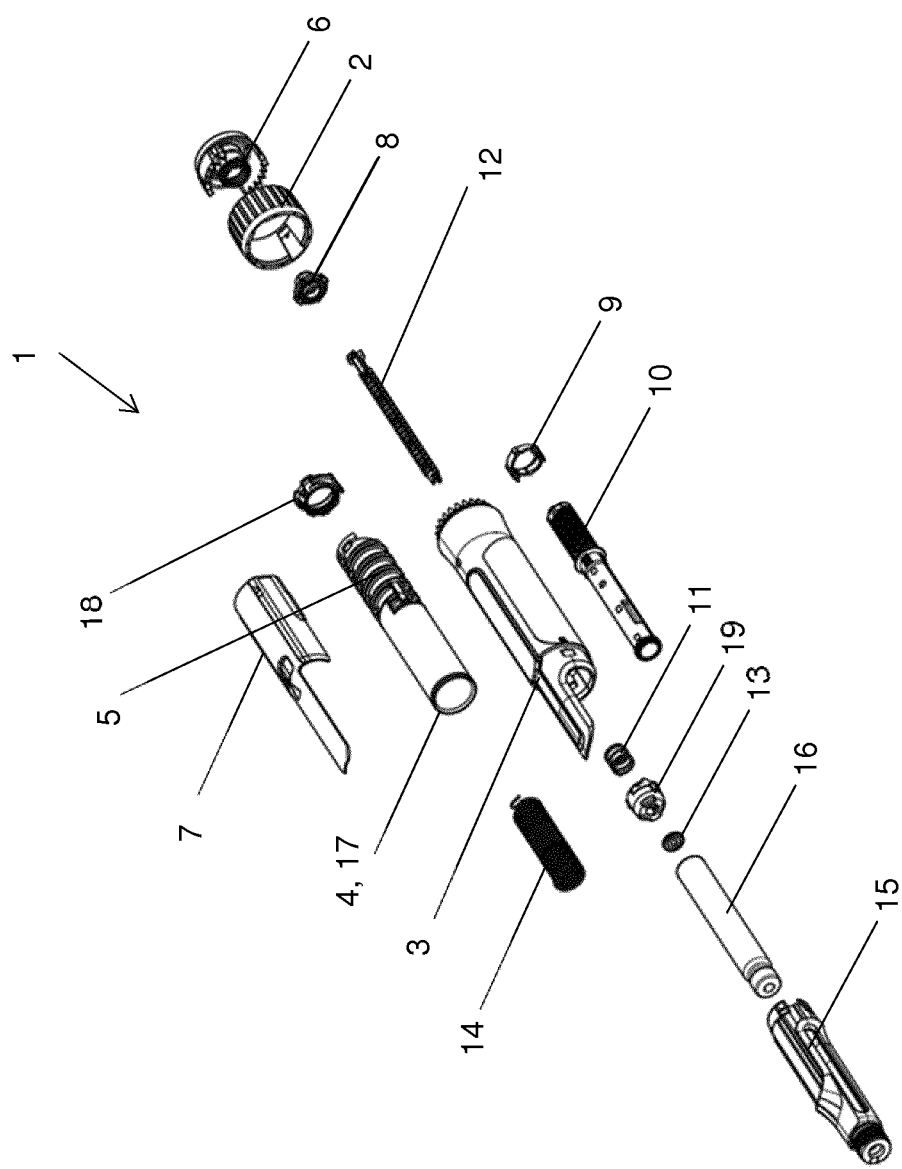
FIG. 1 shows an exploded view of an example of a drug delivery device.

FIG. 1 shows an exploded view of a first embodiment of the injection device 1 with its components which are a dose dial 2 in the form of a dial grip, a housing body 3, a dose setting member in the form of a dose scale drum or number sleeve 4 which has an outer thread 5 on its outer peripheral surface extending in a helical pattern from a distal end to a proximal end.

The dose dial 2 is axially retained in the housing body 3 and the number sleeve 4 is directly coupled to the dial button 2 to follow rotation of the dial button 2 such that when a user rotates the dial button 2 to select a dose, the number sleeve 4 rotates together with the dial button 2. The dial button 2 and the number sleeve 4 are arranged such that they both rotate without any axial displacement. A dispense button 6 is attached to the distal end of the drug delivery device.

The device further comprises a sliding element 7 configured as a gauge component with a sliding window, a clutch plate 8, a last dose nut 9, a drive sleeve 10, a clutch spring 11, a lead screw or piston rod 12, a bearing 13 provided at a distal end of the lead screw 12, a drive spring 14 in the form of a torsion spring, a cartridge holder 15 that can be attached to the distal end of the housing body 3 and that receives a cartridge 16 which is filled with a medicament and which has a bung 20 (see FIG. 2) inside, wherein when the bearing 13 is moved in distal direction the bearing displaces the bung 20 such that medicament is dispensed from the cartridge 16 when a dispense interface such as a double ended needle cannula is attached to the distal end of the cartridge 16. The number sleeve 4 comprises an upper number sleeve part 18 referred to as the number sleeve upper and a lower number sleeve part 17 referred to as the number sleeve lower that are permanently fixed to each other during assembly to simplify number sleeve 4 mould tooling and assembly.

A threaded insert 19 in the form of a threaded nut is accommodated in the housing body 3 and has an inner thread engaging a corresponding threaded on the outer surface of the lead screw 12. Relative rotation between the lead screw 12 and the threaded insert 19 causes relative displacement in axial direction.

The helical drive spring 14 is charged and stores energy during dose setting by the action of the user rotating the dose dial 2. The spring energy is stored until the mechanism is triggered for dispense at which point the energy stored is used to deliver the medicament from the cartridge to the user. The drive spring 14 is attached at one end to the housing body 3 and at the other end to the number sleeve 4. The drive spring 14 is pre-wound upon assembly, such that it applies a torque to the number sleeve 4 when the mechanism is at zero units dialed. The action of rotating the dose dial 2 to set a dose, rotates the number sleeve 4 relative to the housing body 3 and charges the drive spring 14 further. The lead screw 12 is rotationally constrained to the drive sleeve 10 via a splined interface.

Figure 2:
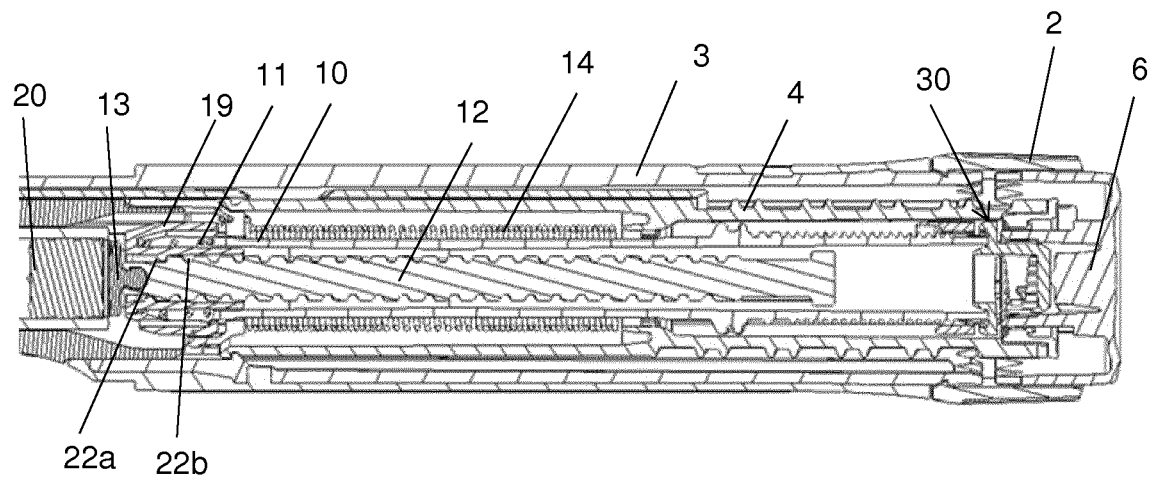
FIG. 2 shows a cut view of a section of the drug delivery device of FIG. 1.

As shown in FIG. 2, the bearing 13 is axially constrained to the lead screw 12 and acts on a bung 20 within the medicament cartridge 16. The threaded insert 19 is constrained in the housing body 3 such that it can rotate through a predetermined angle of rotation on a helical path. A thread engagement (not shown) between the housing body 3 and the threaded insert 19 constitutes a coupling between these elements which translates axial movement of the threaded insert 19 into rotation around a longitudinal axis and induces a torque.

The clutch spring 11 is a compression spring and is arranged between the drive sleeve 10 and the threaded insert 19 such as to bias the threaded insert 19 in distal direction (in a direction towards the cartridge) and such as to bias the drive sleeve 10 in the proximal direction.

Figure 3:
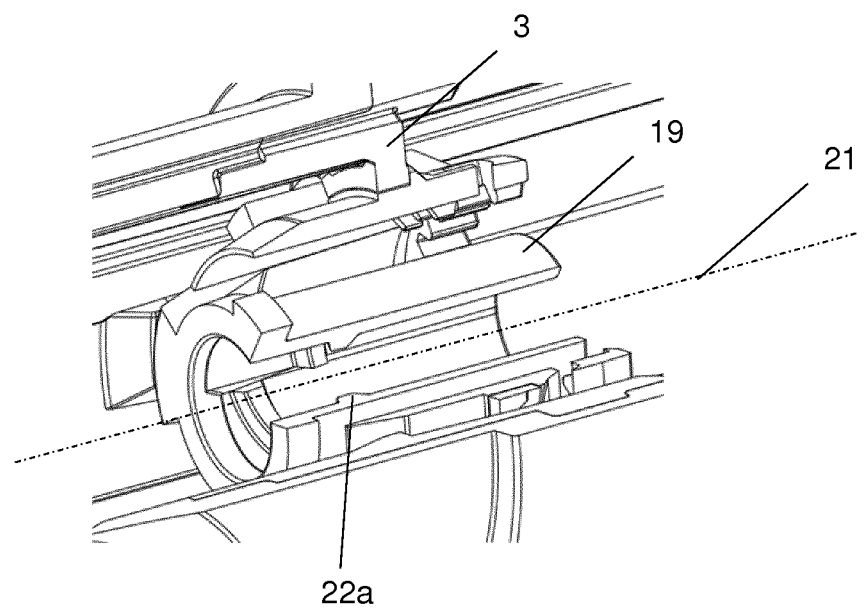
FIG. 3 shows a perspective view of a distal section of the drug delivery device of FIG. 2 with parts removed.

FIG. 3 shows an inner section of the drug delivery device with the piston rod removed. The threaded insert 19 has an opening extending along a longitudinal axis 21 with an inner thread feature 22a for engaging the outer thread 22b of the lead screw 12 as shown in FIG. 2.

Figure 4:
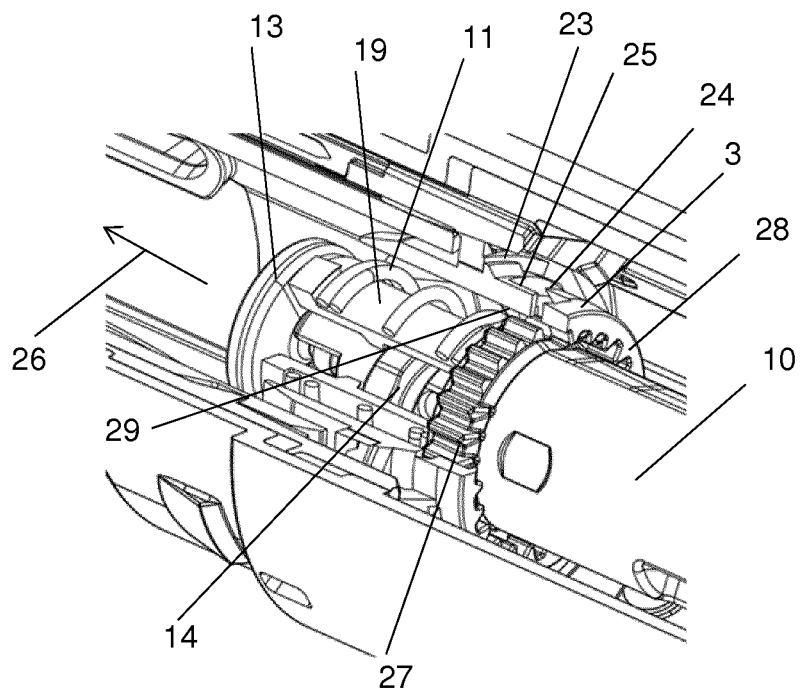
FIG. 4 shows a perspective view of a distal section of the drug delivery device of FIG. 2 in a dose setting state.

FIG. 4 shows the inner section of the drug delivery device of FIG. 3 from another perspective, but with the drive sleeve 10, the clutch spring 11, the piston rod 14 with the bearing 13. In the threaded engagement between the housing body 3 and the threaded insert 19 there are two rotational stops provided by end-of-thread features. As shown in FIG. 4, the clutch spring 11 urges the threaded insert 19 against a helical surface 23 into a rotational stop The threaded insert has a projection surface for engaging said stop. In the opposite direction, there is also provided a rotational stop 24 and a helical stop surface 25 in the housing body 3. The stop 23 defines a position of the threaded insert 19, when the threaded insert abuts the stop means 23. The clutch spring 11 is a resilient means that urges the threaded insert 19 against the stop 23.

The drive sleeve 10 is configured as a selection member and is displaceable in the axial direction between a proximal first axial position and a second distal position. The axial position of the drive sleeve 10, the clutch plate 8 and the button 6 is defined by the action of the clutch spring 11, which applies a force on the drive sleeve 10 in the proximal direction. This spring force is reacted through the threaded insert 19 to the housing body 3. In the 'At rest' position, this spring force ensures that the threaded insert 19 is biased in a distal direction 26 against the stop 23 such that it is held against the housing body 3 in a known axial and rotational position.

On the outer surface of the drive sleeve 10, there is provided a number of extending splines 27 in the form of teeth. On a radial inner surface of the housing body 3, there is provided a number of extending splines 28 in the form of teeth extending inwardly. On a radial inner surface of the threaded insert 19, there is also provided a number of axially extending splines 29 in the form of teeth extending inwardly.

The first axial position of the drive sleeve 10 as shown in FIG. 4 corresponds to a dose setting state. The clutch spring 19 urges the drive sleeve 10 into the first axial position. The splines 27 of the drive sleeve 10 engage the splines 28 of the housing body 3 such that the drive sleeve 10 is locked against rotation. In this dose setting state, a release clutch 30 (see FIG. 2) between the drive sleeve 10 and the number sleeve 4 is not engaged, so that the number sleeve 4 can rotate relative to the drive sleeve 10. Rotation of the dial grip 2 generates an identical rotation in the number sleeve 4. Rotation of the number sleeve 4 causes charging of the drive spring 14, increasing the energy stored within it. The drive sleeve 10 is prevented from rotating as the dose is set and the number sleeve 4 is rotated, due to the engagement of its splined teeth 27 with the teeth 28 of the housing body 3.

An end surface of the drive sleeve 10 is provided with angled teeth to form a ratchet interface with angled teeth on the clutch plate 8. On the outer circumference of the clutch plate 8, splined teeth for engaging a corresponding groove on the number sleeve 4 are formed. The user torque required to rotate the dial grip is a sum of the torque required to wind up the drive spring, and the torque required to overhaul the ratchet feature. The clutch spring is designed to provide an axial force to maintain the ratchet teeth engagement of the clutch plate 8 and the drive sleeve 10. The torque required to overhaul the ratchet in the dose set direction is a function of the axial load applied by the clutch spring, the clockwise ramp angle of the ratchet, the friction coefficient between the mating surfaces and the mean radius of the ratchet features. As the user rotates the dial grip 2 sufficiently to increment the mechanism by one increment, the number sleeve 4 rotates relative to the drive sleeve 10 by one ratchet tooth. At this point the ratchet teeth re-engage into the next detented position. An audible click is generated by the ratchet re-engagement, and tactile feedback is given by the change in torque input required.

With no user torque applied to the dial grip 2, the number sleeve 4 is prevented from rotating back under the torque applied by the drive spring 14, solely by the ratchet engagement between the clutch plate 8 and the drive sleeve 10.

To dispense a set dose, the user presses the button 6. The clutch plate 8 is moved axially by the button and the drive sleeve 10 is moved axially by the clutch plate 8. The dialling clutch interface between the drive sleeve 10 and clutch plate 8 will prevent relative rotation in normal dispense.

In addition (back-up) or as an alternative to this interface a tooth interface may be provided. Axial displacement of the drive sleeve 10 into the distal second axial position engages splines (not shown) on the drive sleeve 10 with splines on the number sleeve 4 so that a splined tooth interface is formed preventing or assisting in preventing relative rotation between the drive sleeve 10 and the number sleeve during dispense.

Figure 5:
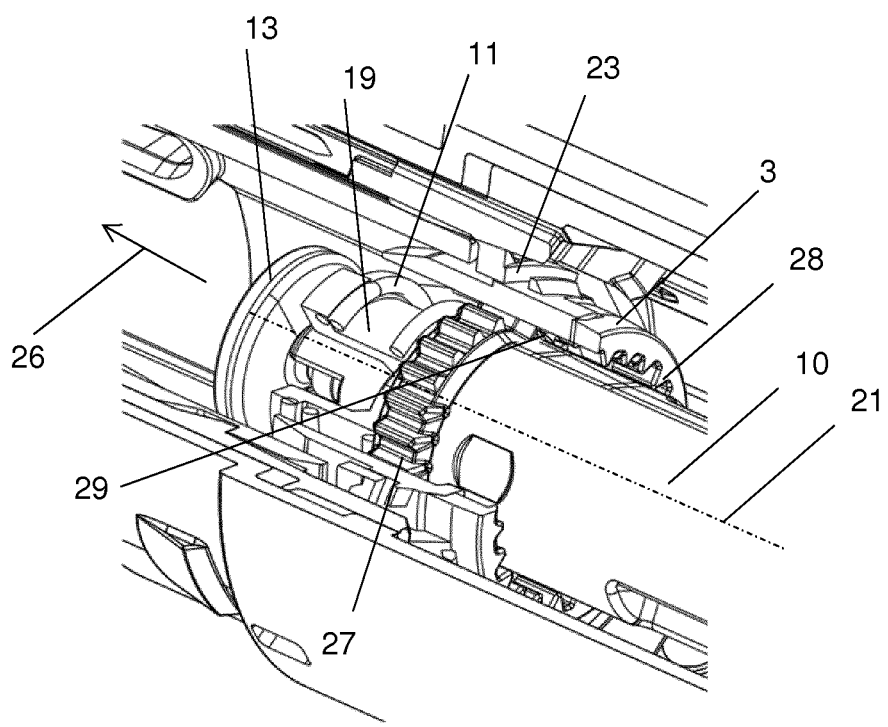
FIG. 5 shows a perspective view of a distal section of the drug delivery device of FIG. 2 in a dose dispensing state.

As shown in FIG. 5, axial displacement of the drive sleeve 10 in distal direction 26 into the second position disengages the splines 27 of the drive sleeve 10 from the splines 28 of the housing 3. When the threaded insert 19 is in the position at the stop 23 as shown in FIG. 4, then the teeth 29 of the threaded insert and the teeth 28 of the housing 3 are aligned so that the teeth 27 of the drive sleeve 10 can pass through the teeth 29 of the threaded insert such that drive sleeve 10 is free to rotate on the force of the drive spring.

Rotation of the drive sleeve 10 causes the lead screw 12 to rotate and the lead screw 12 advances due to its threaded engagement with the threaded insert 19 in the distal direction. When the reaction forces from the cartridge bung acting in proximal direction increase, the threaded insert 19 is biased in proximal direction and rotationally against the thread of the lead screw 12 as shown in FIG. 5.

Due to the helical thread engagement between the threaded insert 19 and the housing body 3, the proximal movement of the threaded insert 19 induces a torque and a rotational movement in a direction around the longitudinal axis 21 that opposes that of the lead screw 12 thread. The threaded insert 19 rotates by approximately half a unit causing a misalignment between teeth 29 on the threaded insert 19 and the teeth 28 on the housing body 3. Delivery of a dose continues while the user continues to depress the button.

When a 0 Units stop between the number sleeve 4 and the gauge component 7 is engaged, delivery of a dose is completed by the clutch spring 11 force axially displacing the threaded insert 19 in distal direction 26 against the helical stop surface 23 on the housing body 3 to induce a rotational movement of the threaded insert 19 forcing it back to its original starting position. The lead screw 12 is prevented from rotating by the drive sleeve 10, which is locked by the number sleeve and the '0 Stop' position, therefore, the threaded contact between the threaded insert 19 and the lead screw 12 causes the lead screw 12 to advance axially until the threaded insert 19 abuts against the stop 23. When the threaded insert 19 is moved back to its original position, the teeth 28 and 29 of the threaded insert 19 and the housing body 3 are realigned. When the user releases the button, the drive sleeve 10 re-engages with the threaded insert 19 and housing body 3. The mechanism is now returned to the 'At rest' condition.

Figure 6:
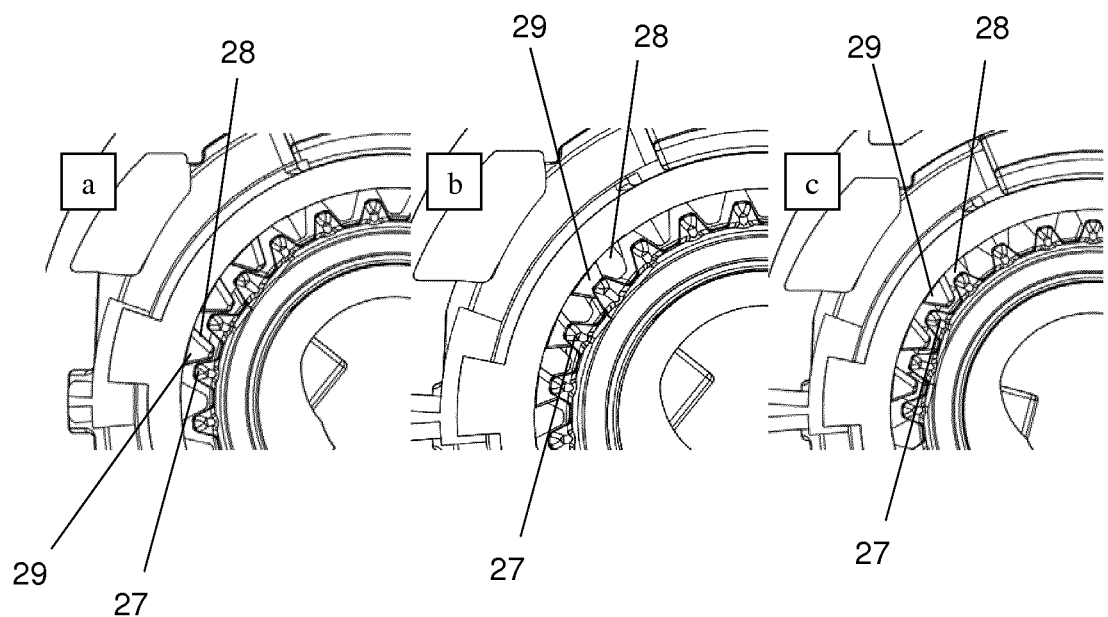
FIGS. 6a-c show cut views along a longitudinal axis of a distal section of the drug delivery device of FIG. 2.

FIG. 6a shows three different scenarios of dispense. FIG. 6a shows the drug delivery in the 'At rest' condition with the teeth 28 and 29 of the threaded insert 19 and the housing body 3 aligned to such degree that the teeth 27 of the drive sleeve can be disengaged as shown in FIG. 5. In FIG. 6a, the teeth 27 of the drive sleeve 10 are splined to the housing body 3.

FIG. 6b shows the teeth 27 of the drive sleeve 10 disengaged from the housing body 3. Rotational movement of the threaded insert 19 due to the reaction forces induced from the bung causes the threaded insert 19 to displace axially and to rotate when the reaction forces overcome the biasing force of the clutch spring. In this state, the teeth 28 of the housing body 3 and the teeth 29 of the threaded insert 19 become misaligned.

In a 'blocked needle' scenario (FIG. 6c) when the 0U is engaged, the reaction force generated by the drive spring through the lead screw to the cartridge bung will remain greater than the force being applied by the clutch spring because the fluid cannot be released through the needle to relieve the pressure and force applied to the bung. This will act to prevent the threaded insert 19 from returning to its 'At rest' position. If the user releases the button, the clutch spring 11 pushes the drive sleeve 10 in a proximal direction. As the teeth 28, 29 of threaded insert 19 and housing body 2 are misaligned when the threaded insert is not at its stop position as shown in FIG. 4, the drive sleeve 10 cannot re-engage with the housing body teeth 27. The drive sleeve engages with the threaded insert 19 and is splined thereto.

As the drive sleeve 10 is prevented from fully returning, the button does not fully return either. In addition, in this condition the button will be able to float axially (i.e. rattle) as there is no longer any biasing force acting on the button.

As the drive sleeve 10 has been prevented from moving proximally to its 'At rest' position, the splined connection between the drive sleeve 10 to the number sleeve 4 has not been released, leaving the device in a locked condition where by the dial grip 2, number sleeve 4, threaded insert 19, drive sleeve 10 and housing body 3 are all splined together preventing the user from dialing. In addition, the button 6 does not fully pop out. This provides additional tactile and visual feedback to the user.

To release the device from a blocked needle condition, a new needle must be fitted to relieve the pressure within the cartridge induced by the drive spring torque being applied through the system. Once the reaction force from the bung (applied through the lead screw) reduces to the required level, the clutch spring force is again able to complete the movement of the lead screw by displacing the threaded insert to its 'At rest' position. Once the threaded insert and the housing body teeth are realigned, the drive sleeve is then also able to return to its 'At rest' position. In this way the mechanism will be returned to an operable condition and the user can dial subsequent doses (assuming sufficient cartridge contents to do so).

Figure 7A:
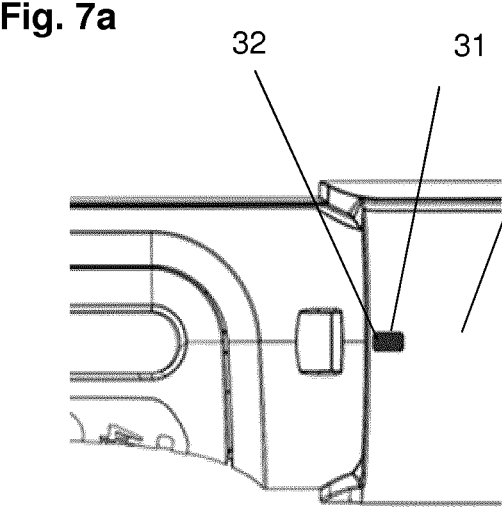
FIGS. 7a, b show side views of a section of the drug delivery device of FIG. 2 in different states.
Figure 7B:
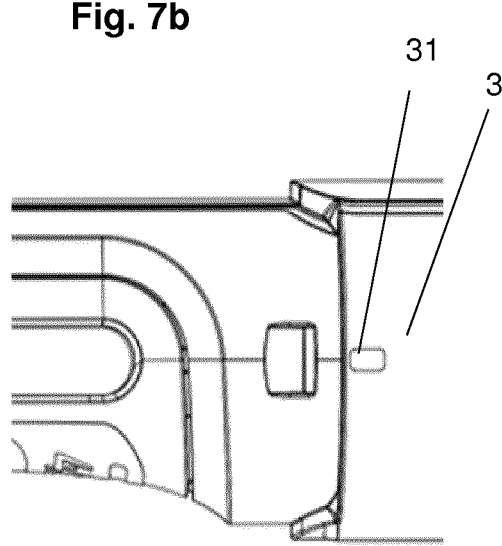

FIGS. 7a and 7b show in side views a section of the drug delivery device with a window 31 provided in the housing body 3. The threaded insert 19 is provided with a colored marking 32.

The window 31 provides additional visual feedback to a user regarding the dosing state of the device via the colored feature 32 on the threaded insert such that during the rotation of the threaded insert, a visual 'flag' (e.g. coloured area) is displayed to the user through a small access window in the housing body 3. During a dosing event, while the threaded insert is in it's rotated position, this 'flag' would be visible (FIG. 7a) but when the threaded insert returns to is 'At rest' position following a successful dosing event it would disappear once again, thereby confirming that the dose had been delivered. In the event of a blocked needle condition, this 'flag' 32 would remain visible in the window 31, helping to highlight that dose delivery has not been completed. It would remain in this state until such time as the pressure in the cartridge were relieved (e.g. by the user fitting a new, un-blocked needle to the device).

If desirable, the rotational size of the 'flag' could be further increased by increasing the angle of rotation defined by the engagement between the threaded insert and the housing body, e.g. by the ramp angles, or by increasing the size of the dose required to fully set the 'flag'. If a very large angle of rotation is desirable, additional torque may be required to ensure that the threaded insert is always able to return to its 'at rest' position following dose completion. This additional torque may be provided by either an additional component (e.g. such as a torsion cantilever or compression spring) or a flexible feature within the threaded insert or housing body.

An alternative embodiment may provide visual feedback only with no mechanical lockout, using a similar component to the threaded insert which interacts with the lead screw but not with the drive sleeve. This would permit modification of the ramp angles between the threaded insert and the housing body to induce a larger rotational movement of the component. A corresponding increase in the size of the window in the housing body could provide stronger visual feedback. With this embodiment, in a blocked needle condition, the drive sleeve and hence the button, are able to return as normal. The device will function as normal, but the 'flag' will remain red. The number of units that the number sleeve winds down in a blocked needle condition will be slightly increased with this concept, because the threaded insert rotation adds flexibility to the system. This applies to all concepts where the threaded insert moves axially or rotationally.

REFERENCE NUMERALS 1 drug delivery device (injection device)
2 dose dial
3 housing body
4 number sleeve (dose setting member)
5 outer thread
6 dispense button
7 sliding element (gauge component)
8 clutch plate
9 last dose nut
10 drive sleeve (selection member)
11 clutch spring
12 lead screw (piston rod)
13 bearing
14 drive spring
15 cartridge holder
16 cartridge
17 number sleeve lower
18 number sleeve upper
19 threaded insert (threaded nut)
20 bung
21 longitudinal axis
22a inner thread feature
22b outer thread
23 stop (helical surface)
24 rotational stop
25 helical stop surface
26 distal direction
27 outer splines of drive sleeve
28 inner splines of housing
29 inner splines of threaded insert
30 release clutch
31 window
32 flag

The invention claimed is:

1. A drug delivery device comprising:
   a housing body;
   a piston rod configured to rotate in a rotational direction during dose dispensing under a driving torque; and
   a threaded insert,
   wherein the piston rod is in threaded engagement with the threaded insert such that during the dose dispensing, the piston rod displaces axially in a distal direction relative to the threaded insert, characterized in that the threaded insert is movable relative to a stop provided in the housing body and that a resilient means is provided to bias the threaded insert against the stop so that the rotation of the piston rod causes the threaded insert to move away from the stop in response to reaction forces, induced by a cartridge bung into the threaded insert, acting on the piston rod in a proximal direction when the reaction forces exceed a biasing force of the resilient means.

2. The drug delivery device according to claim 1, wherein the threaded insert is prestressed against the stop by the resilient means.

3. The drug delivery device according to claim 1, wherein the resilient means comprises a spring.

4. The drug delivery device according to claim 1, wherein the stop comprises an axial stop or a rotational stop and wherein the resilient means is configured to bias the threaded insert against one or both of the axial stop or the rotational stop.

5. The drug delivery device according to claim 1, wherein the threaded insert is constrained in the housing body such as to be able to rotate through a predetermined angle of rotation on a helical path relative to the stop.

6. The drug delivery device according to claim 1, comprising:
   a drive sleeve configured to rotate the piston rod during the dose dispensing;
   a power reservoir operably coupled to the drive sleeve such as to rotate the drive sleeve upon release of energy stored in the power reservoir;
   a dose setting member configured to charge the power reservoir upon rotation;
   a release clutch arranged between the drive sleeve and the dose setting member, wherein the release clutch is configured to allow relative rotation of the dose setting member and the drive sleeve during dose setting and to rotationally constrain the drive sleeve to the dose setting member during the dose dispensing; and a selection member axially moveable relative to the housing body between a first axial position and a second axial position, wherein the selection member is operably coupled to the drive sleeve such that in the first axial position of the selection member, the drive sleeve is disengaged from the dose setting member and such that in the second axial position of the selection member, the drive sleeve is rotationally constrained to the dose setting member, wherein the threaded insert is configured such that when the threaded insert is in a position away from the stop, the threaded insert prevents the selection member from returning to the first axial position.

7. The drug delivery device according to claim 6, wherein the selection member is configured to engage the housing body in the first axial position such that the drive sleeve is rotationally constrained to the housing body, and wherein in the second axial position, the drive sleeve is rotatable relative to the housing body.

8. The drug delivery device according to claim 6, comprising a dispense or trigger button for displacing the selection member from the first axial position into the second axial position.

9. The drug delivery device according to claim 6, wherein the selection member is configured as the drive sleeve.

10. The drug delivery device according to claim 9, wherein the resilient means is arranged such as to bias the drive sleeve into the first axial position.

11. The drug delivery device according to claim 9, wherein the drive sleeve, the threaded insert and the housing body are each provided with spline features, wherein axial displacement of the drive sleeve from the first axial position into the second axial position causes disengagement of the spline features of the drive sleeve from the spline features of the housing body through the spline features of the threaded insert such that the drive sleeve is free to rotate, wherein displacement of the threaded insert away from the stop causes misalignment between the spline features of the threaded insert and the housing body such that the drive sleeve is prevented from returning into the first axial position.

12. The drug delivery device according to claim 6, wherein the threaded insert is configured to engage and to rotationally lock the drive sleeve to the threaded insert when the threaded insert is in the position away from the stop and when the drive sleeve is returned from the second axial position towards the first axial position.

13. The drug delivery device according to claim 1, further comprising means to provide one or more of a haptic feedback, a visual feedback, or a tactile feedback when the threaded insert is displaced.

14. The drug delivery device according to claim 13, wherein the housing body is provided with a window or an aperture arranged to provide visual confirmation of the displacement of the threaded insert.

15. The drug delivery device according to claim 1, further comprising a cartridge containing a medicament, the cartridge being located in the distal direction in front of the piston rod thereby allowing the cartridge bung inside the cartridge to be displaced along the distal direction by contact to the piston rod when advancing.

* * * * *

UNITED STATES PATENT AND TRADEMARK OFFICE
CERTIFICATE OF CORRECTION

| | |
|---|---|
| PATENT NO. | : 11,406,762 B2 |
| APPLICATION NO. | : 16/312204 |
| DATED | : August 9, 2022 |
| INVENTOR(S) | : Markus Ploch et al. |

It is certified that error appears in the above-identified patent and that said Letters Patent is hereby corrected as shown below:

On the Title Page

Column 2, Line 5 under item (57) ABSTRACT, delete "dispensing." and insert -- dispensing, --

Column 2, Line 7 under item (57) ABSTRACT, delete "hung." and insert -- bung. --

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 41

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
<220> FEATURE:
<223> OTHER INFORMATION: H-(Lys)4-des Pro36, des Pro37 Exendin-4(1-39)-
      NH2

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: H-(Lys)5-des Pro36, des Pro37 Exendin-4(1-39)-
      NH2

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 38
<212> TYPE: PRT
<213> ORGANISM: Artificial Sequence
<220> FEATURE:
<223> OTHER INFORMATION: des Pro36 [IsoAsp28] Exendin-4(1-39)
<220> FEATURE:
<221> NAME/KEY: MOD_RES
<222> LOCATION: (28)..(28)
<223> OTHER INFORMATION: X=isoaspartate

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MOD_RES
<222> LOCATION: (14)..(14)
<223> OTHER INFORMATION: X=methionine oxide

<400> SEQUENCE: 7

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MOD_RES
<222> LOCATION: (14)..(14)
<223> OTHER INFORMATION: X=methionine oxide
<220> FEATURE:
<221> NAME/KEY: MOD_RES

```
<222> LOCATION: (28)..(28)
<223> OTHER INFORMATION: X=isoaspartate

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MOD_RES
<222> LOCATION: (25)..(25)
<223> OTHER INFORMATION: X=tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: des Pro36 [Trp(O2)25, IsoAsp28] Exendin-4(1-39)
<220> FEATURE:
<221> NAME/KEY: MOD_RES
<222> LOCATION: (25)..(25)
<223> OTHER INFORMATION: X=tryptophan dioxide
<220> FEATURE:
<221> NAME/KEY: MOD_RES
<222> LOCATION: (28)..(28)
<223> OTHER INFORMATION: X=isoaspartate

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, Asp28] Exendin-
      4(1-39)
<220> FEATURE:
<221> NAME/KEY: MOD_RES
<222> LOCATION: (14)..(14)
<223> OTHER INFORMATION: X=methionine oxide
<220> FEATURE:
<221> NAME/KEY: MOD_RES
<222> LOCATION: (25)..(25)
```

<223> OTHER INFORMATION: X=tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MOD_RES
<222> LOCATION: (14)..(14)
<223> OTHER INFORMATION: X=methionine oxide
<220> FEATURE:
<221> NAME/KEY: MOD_RES
<222> LOCATION: (25)..(25)
<223> OTHER INFORMATION: X=tryptophan dioxide
<220> FEATURE:
<221> NAME/KEY: MOD_RES
<222> LOCATION: (28)..(28)
<223> OTHER INFORMATION: X=isoapartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Lys Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 14
<211> LENGTH: 50
<212> TYPE: PRT
<213> ORGANISM: Artificial Sequence
<220> FEATURE:
<223> OTHER INFORMATION: H-(Lys)6-des Pro36 [Asp28] Exendin-4(1-39)-
      Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu

```
                    20                  25                  30

Lys Asp Gly Gly Pro Ser Ser Gly Ala Pro Pro Ser Lys Lys Lys Lys
            35                  40                  45

Lys Lys
    50

<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37, Pro38Exendin-4(1-39)-
      NH2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35

<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28] Exendin-4(1-
      39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
      Exendin-4(1-39)-NH2

<400> SEQUENCE: 17

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28] Exendin-4(1-
      39)-(Lys)6-NH2

<400> SEQUENCE: 18
```

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40
```

<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
      Exendin-4(1-39)-(Lys)6-NH2

<400> SEQUENCE: 19

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50
```

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
      Exendin-4(1-39)-(Lys)6-NH2

<400> SEQUENCE: 20

```
Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50
```

<210> SEQ ID NO 21
<211> LENGTH: 50
<212> TYPE: PRT
<213> ORGANISM: Artificial Sequence
<220> FEATURE:
<223> OTHER INFORMATION: H-(Lys)6-des Pro36 [Trp(O2)25, Asp28] Exendin-
      4(1-39)-Lys6-NH2
<220> FEATURE:
<221> NAME/KEY: MOD_RES
<222> LOCATION: (31)..(31)
<223> OTHER INFORMATION: X=tryptophan dioxide

<400> SEQUENCE: 21

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45
```

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MOD_RES
<222> LOCATION: (25)..(25)
<223> OTHER INFORMATION: X=tryptophan dioxide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MOD_RES
<222> LOCATION: (31)..(31)
<223> OTHER INFORMATION: X=tryptophan dioxide

<400> SEQUENCE: 23

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 24
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-NH2
<220> FEATURE:
<221> NAME/KEY: MOD_RES
<222> LOCATION: (31)..(31)
<223> OTHER INFORMATION: X=tryptophan dioxide

<400> SEQUENCE: 24

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 25
<211> LENGTH: 44
<212> TYPE: PRT

```
<213> ORGANISM: Artificial Sequence
<220> FEATURE:
<223> OTHER INFORMATION: des Pro36, Pro37, Pro38 [Trp(O2)25, Asp28]
      Exendin-4(1-39)-(Lys)6-NH2
<220> FEATURE:
<221> NAME/KEY: MOD_RES
<222> LOCATION: (25)..(25)
<223> OTHER INFORMATION: X=tryptophan dioxide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
            35                  40

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-(Lys)6-NH2
<220> FEATURE:
<221> NAME/KEY: MOD_RES
<222> LOCATION: (31)..(31)
<223> OTHER INFORMATION: X=tryptophan dioxide

<400> SEQUENCE: 26

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
            35                  40                  45

Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-(Lys)6-NH2
<220> FEATURE:
<221> NAME/KEY: MOD_RES
<222> LOCATION: (31)..(31)
<223> OTHER INFORMATION: X=tryptophan dioxide

<400> SEQUENCE: 27

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
            35                  40                  45

Lys Lys
    50

<210> SEQ ID NO 28
<211> LENGTH: 50
<212> TYPE: PRT
<213> ORGANISM: Artificial Sequence
```

-continued

```
<220> FEATURE:
<223> OTHER INFORMATION: H-(Lys)6-des Pro36 [Met(O)14, Asp28] Exendin-
      4(1-39)-Lys6-NH2
<220> FEATURE:
<221> NAME/KEY: MOD_RES
<222> LOCATION: (20)..(20)
<223> OTHER INFORMATION: X=methionine oxide

<400> SEQUENCE: 28

Lys Lys Lys Lys Lys Lys His Gly Glu Gly Thr Phe Thr Ser Asp Leu
1               5                  10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION: des Met(O)14 Asp28 Pro36, Pro37, Pro38 Exendin-
      4(1-39)-NH2

<400> SEQUENCE: 29

His Gly Glu Gly Thr Phe Thr Ser Asp Leu Ser Lys Gln Glu Glu Glu
1               5                  10                  15

Ala Val Arg Leu Phe Ile Glu Trp Leu Lys Asp Gly Gly Pro Ser Ser
            20                  25                  30

Gly Ala Pro Pro Pro Ser
        35

<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X=methionine oxide

<400> SEQUENCE: 30

Lys Lys Lys Lys Lys Lys His Gly Glu Gly Thr Phe Thr Ser Asp Leu
1               5                  10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X=methionine oxide
```

<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
      Exendin-4(1-39)-(Lys)6-NH2
<220> FEATURE:
<221> NAME/KEY: MOD_RES
<222> LOCATION: (14)..(14)
<223> OTHER INFORMATION: X=methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-(Lys)6-NH2
<220> FEATURE:
<221> NAME/KEY: MOD_RES
<222> LOCATION: (20)..(20)
<223> OTHER INFORMATION: X=methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 34
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14,
      Asp28] Exendin-4(1-39)-(Lys)6-NH2
<220> FEATURE:
<221> NAME/KEY: MOD_RES
<222> LOCATION: (20)..(20)
<223> OTHER INFORMATION: X=methionine oxide

<400> SEQUENCE: 34

Asn Glu Glu Glu Glu Glu His Gly Glu Gly Thr Phe Thr Ser Asp Leu
1               5                   10                  15

```
Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28]
      Exendin-4(1-39)-Lys6-NH2
<220> FEATURE:
<221> NAME/KEY: MOD_RES
<222> LOCATION: (20)..(20)
<223> OTHER INFORMATION: X=methionine oxide
<220> FEATURE:
<221> NAME/KEY: MOD_RES
<222> LOCATION: (31)..(31)
<223> OTHER INFORMATION: X=tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14,
      Trp(O2)25] Exendin-4(1-39)-NH2
<220> FEATURE:
<221> NAME/KEY: MOD_RES
<222> LOCATION: (14)..(14)
<223> OTHER INFORMATION: X=methionine oxide
<220> FEATURE:
<221> NAME/KEY: MOD_RES
<222> LOCATION: (25)..(25)
<223> OTHER INFORMATION: X=tryptophan oxide

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 37
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-NH2
<220> FEATURE:
<221> NAME/KEY: MOD_RES
```

```
<222> LOCATION: (20)..(20)
<223> OTHER INFORMATION: X=methionine oxide

<400> SEQUENCE: 37

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 38
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MOD_RES
<222> LOCATION: (20)..(20)
<223> OTHER INFORMATION: X=methionine oxide
<220> FEATURE:
<221> NAME/KEY: MOD_RES
<222> LOCATION: (31)..(31)
<223> OTHER INFORMATION: X=tryptophan oxide

<400> SEQUENCE: 38

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 39
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MOD_RES
<222> LOCATION: (14)..(14)
<223> OTHER INFORMATION: X=methionine oxide
<220> FEATURE:
<221> NAME/KEY: MOD_RES
<222> LOCATION: (25)..(25)
<223> OTHER INFORMATION: X=tryptophan oxide

<400> SEQUENCE: 39

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 40
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
```

```
<221> NAME/KEY: MOD_RES
<222> LOCATION: (20)..(20)
<223> OTHER INFORMATION: X=methionine oxide
<220> FEATURE:
<221> NAME/KEY: MOD_RES
<222> LOCATION: (31)..(31)
<223> OTHER INFORMATION: X=tryptophan oxide

<400> SEQUENCE: 40

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 41
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MOD_RES
<222> LOCATION: (20)..(20)
<223> OTHER INFORMATION: X=methionine oxide
<220> FEATURE:
<221> NAME/KEY: MOD_RES
<222> LOCATION: (31)..(31)
<223> OTHER INFORMATION: X=tryptophan oxide

<400> SEQUENCE: 41

Asn Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50
```